US00PP08029P

United States Patent [19]

Hanes

[11] Patent Number: Plant 8,029

[45] Date of Patent: Nov. 10, 1992

[54] GERANIUM NAMED AMERICANA PINK

[75] Inventor: Mitchell Hanes, Morgan Hill, Calif.

[73] Assignee: Goldsmith Seeds, Inc., Gilroy, Calif.

[21] Appl. No.: 656,709

[22] Filed: Feb. 19, 1991

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

A new Geranium plant particularly distinguished by its abundant foliage and its large semi-double pink colored flowers. The flower clusters consist of about forty florets each of which has a diameter of about 4.5 centimeters; the plant being free flowering and fast-rooting. The plant is quite spectacular in the balance of inflorescence to plant mass, with the relatively short peduncles placing the unusually large, colorful umbels just atop the foilage.

1 Drawing Sheet

BACKGROUND

The present invention comprises a new and distinct geranium cultivar, botanically known as *Pelargonium hortorum* Bailey. The new cultivar is propagated from a seedling resulting from the cross of a seed parent "Casino" (patent pending) and the pollen parent "Blues" (U.S. Plant Pat. No. 5,373).

This new geranium cultivar is a product of a planned breeding program intended to create new plants with pink colored flowers in semi-double flower form, green foliage, vigorous growth and superior cutting productivity.

The new cultivar was created in 1988 in Gilroy, Calif. and has been repeatedly asexually reproduced by cuttings in Gilroy, Calif. and Guatemala over a two year period. It has also been trialed at Okemos, Mich. It has been found to retain its distinctive characteristics through successive propagations; and this novelty appears to be firmly fixed.

DESCRIPTION OF THE DRAWING

This new Geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVARS

The following detailed descriptions set forth the distinctive characteristics of this new geranium. The data which defines these characteristics were collected from asexual reproductions carried out in Gilroy, Calif. The plant history was taken on 20 week old plants, blossomed under natural light in a greenhouse and color readings were taken in the greenhouse on May 29, 1990 at 2:00 P.M. under ambient light. Color references are primarily to The R.H.S. Colour Chart of The Royal Horticultural Society of London, England.

THE PLANT

Classification:

*Botanical.*—*Pelargonium hortorum* Bailey.

*Commercial.*—Zonal geranium.

Form: Intermediate height bush form.

Height: Nine to eleven cm., as a 5½ inch pot plant, excluding blooms.

Growth: Vigorous growth; free flowering and fast-rooting.

Strength: Sturdy not susceptible to wind or rain damage. Good shipping ability as rooted or unrooted cuttings.

Foliage: Abundant quantity.

*Leaves.*—Size: Diameter about 6 cm. Shape: Rounded cordate with occasional upfolding between veins. Margin: Irregularly crenate. Texture: Leathery and pubescent on both surfaces, especially along veins. Ribs and veins: Distinctly palmate, 3 to 4 cm. long. Color: Upper side: Green. Underside: Lighter green color. Ribs and veins not prominently different from upper surface.

*Petioles.*—About 3.8 to 6.0 cm. in length.

THE BUD

Size:

*Diameter.*—About 7 mm.

*Length.*—About 1.7 cm. to 2.0 cm. at time of bud opening.

Shape: Pointed ovoid.

Color: When sepals first divide, RHS 66-D.

Sepals: Five in number, flat behind petals. Pointed linear lanceolate, RHS 67-C/D in an open flower.

THE FLOWER

Blooming habit: Continuous throughout the year.

Size: Approximately 4.5 cm. diameter, 1.3 cm. deep, irregularly radially symmetrical.

Form: Cup-shaped when bloom first opens, later flattening to shallow cup shape with maturity.

Petals: Five to six imbricate outer petals, 2.2–2.5 cm. wide and approximately 2.4 cm. long, 2 to 4 inner smaller petaloids of varying shape. Both the outer petals and inner petaloids are pink, RHS 67-C/D. Veins are not distinctly darker than interveinal regions. Color changing little with age. Underside of petals lighter and veins darker than interveinal regions. Petals and petaloids soft and satiny. Petal and petaloid coloration includes splashes of white or lighter pink shades radiating from the basal portions of the two top outer petals of most florets: where veining is of conspicuously darker coloration than interveinal areas. Whiter portions of such petals normally is confined to about the lower ⅓ central portion of the top two petals of florets, and is diffused gradually with a progressively more intense pink blush toward petal margins. The reverse surfaces of the petals and petaloids may include white shadings or lighter, faded pink shadings, which vary in intensity, and may starkly contrast with a generally solid and uniform pink of the top surfaces. Except for the two top petals, the remaining petals and petaloids generally appear solid in pink coloration rendering an overall lively pink and pink-white character to the massive mound-shaped umbels.

Pedicel: Approximately 3 cm. in length.

Persistence: Nonshattering flower.

INFLORESCENSE

Type: An umbel composed of approximately 40 flowers, erect or laterally ascending.

Peduncle: Approximately 5–8 cm. in length, mostly 8 cm; green in color. The peduncles are naturally short, not having been treated with growth regulators.

REPRODUCTIVE ORGANS

Stamens:

*Anthers.*—Eight to ten positioned below the mature stigma, dull red prior to anthesis.

*Filaments.*—White from base turning red near the point of connection to the anther.

*Pollen.*—Orange in color.

Pistil:

*Number.*—One.

*Length.*—Approximately 7 mm.

*Stigma.*—Five (sometimes six) linear lobes of near equal length, curling back toward ovary, purplish-red.

*Style.*—Length: about 3–3.5 mm. color: purplish red.

*Ovaries.*—At anthesis, densely pubescent with white hairs, oblong. Green drying to a light brown at maturity.

*Fruit.*—Partially fertile.

I claim:

1. A new and distinct cultivar of Geranium substantially as herein shown and described characterized by green foilage with pink colored with splashes of white and light pink semi-double flowers on large umbels held just above the foilage by relatively short peduncles, the plant being fast-rooting and having a vigorous bush like growth habit.

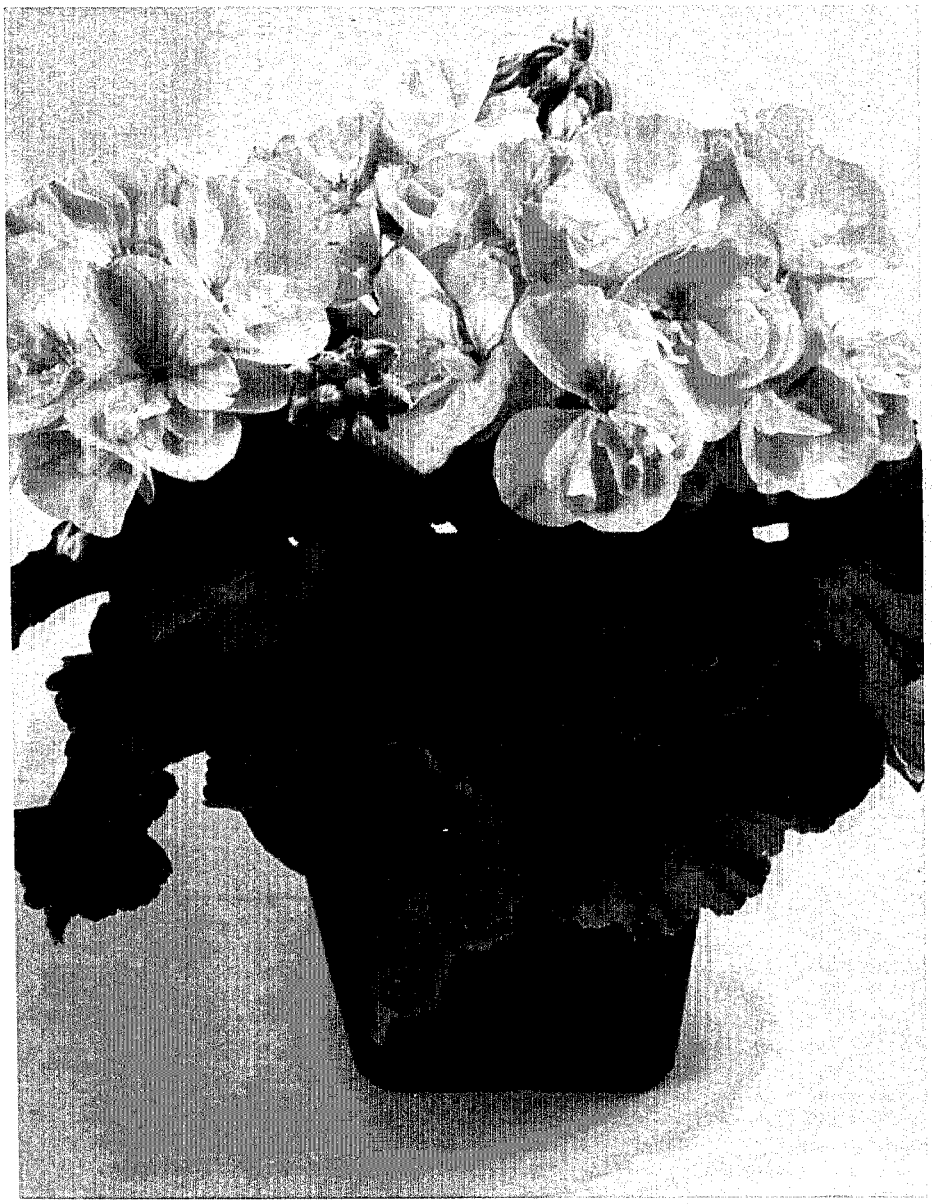

* * * * *